United States Patent [19]

Heavner, Jr. et al.

[11] 4,027,664
[45] June 7, 1977

[54] DIAGNOSTIC ELECTRODE ASSEMBLY WITH A SKIN PREPARATION SURFACE

[75] Inventors: Paul William Heavner, Jr., Kettering, Ohio; Gregor Dean Long, Libertyville, Ill.

[73] Assignee: Baxter Travenol Laboratories, Inc., Deerfield, Ill.

[22] Filed: Nov. 17, 1975

[21] Appl. No.: 632,740

[52] U.S. Cl. .................. 128/2.06 E; 128/2.1 E; 128/DIG. 4; 128/417
[51] Int. Cl.² .......................................... A61B 5/04
[58] Field of Search .......... 128/2.06 E, 2.1 E, 404, 128/410, 411, 416, 417, 418, 272, DIG. 4; 51/407

[56] References Cited

UNITED STATES PATENTS

| | | | |
|---|---|---|---|
| 2,838,891 | 6/1958 | Haywood | 51/407 |
| 2,866,452 | 12/1958 | Laub | 128/2 |
| 2,887,112 | 5/1959 | Smith | 128/417 |
| 2,924,219 | 2/1960 | Wershaw | 128/260 |
| 3,747,590 | 7/1973 | Motley | 128/2.06 E |
| 3,805,769 | 4/1974 | Sessions | 128/2.06 E |
| 3,830,227 | 8/1974 | Green | 128/2.06 E X |
| 3,882,853 | 5/1975 | Gofman et al. | 128/2.06 E |
| 3,901,218 | 8/1975 | Buchalter | 128/2.06 E |
| 3,911,906 | 10/1975 | Reinhold, Jr. | 128/2.06 E |

Primary Examiner—Robert W. Michell
Assistant Examiner—Lee S. Cohen
Attorney, Agent, or Firm—Eugene M. Cummings; Paul C. Flattery

[57] ABSTRACT

A disposable electrode assembly for establishing electrical contact with an underlying skin surface includes a relatively thin base member having a central hub portion and an adhesive-coated undersurface, a conductive gel-impregnated sponge contact contained in a downwardly facing recess located in the hub, and a relatively thick and inflexible cover member coextensive with the base member. In storage the cover member is attached to the undersurface of the base member by the adhesive and the sponge is confined within the recess. Prior to use the base member is peeled away from the cover member to expose the adhesive surface, which when applied to a skin surface holds the sponge contact in compression-contact therewith. The cover member includes a roughened surface about its circumference for cleaning the skin surface prior to applying the base member to the skin.

8 Claims, 7 Drawing Figures

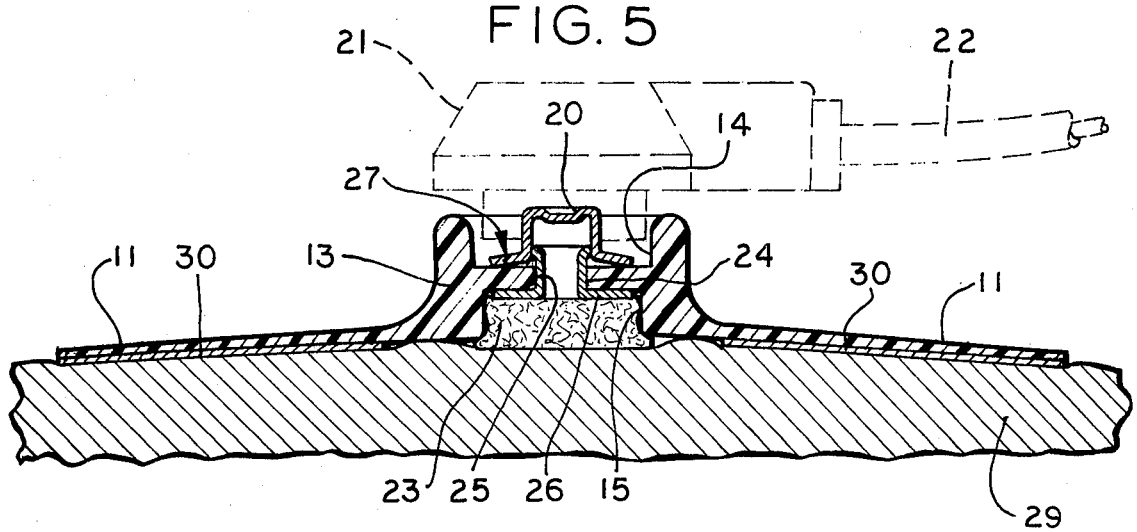
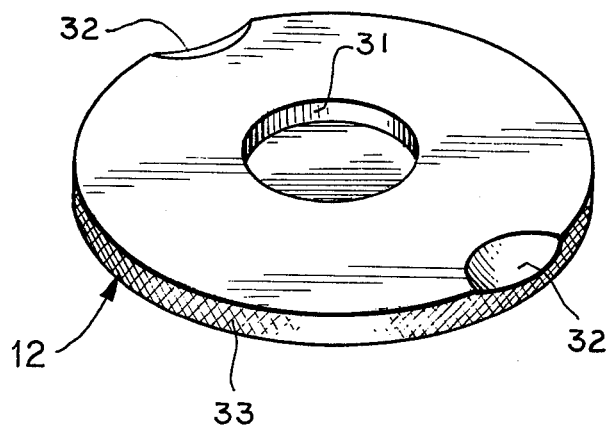
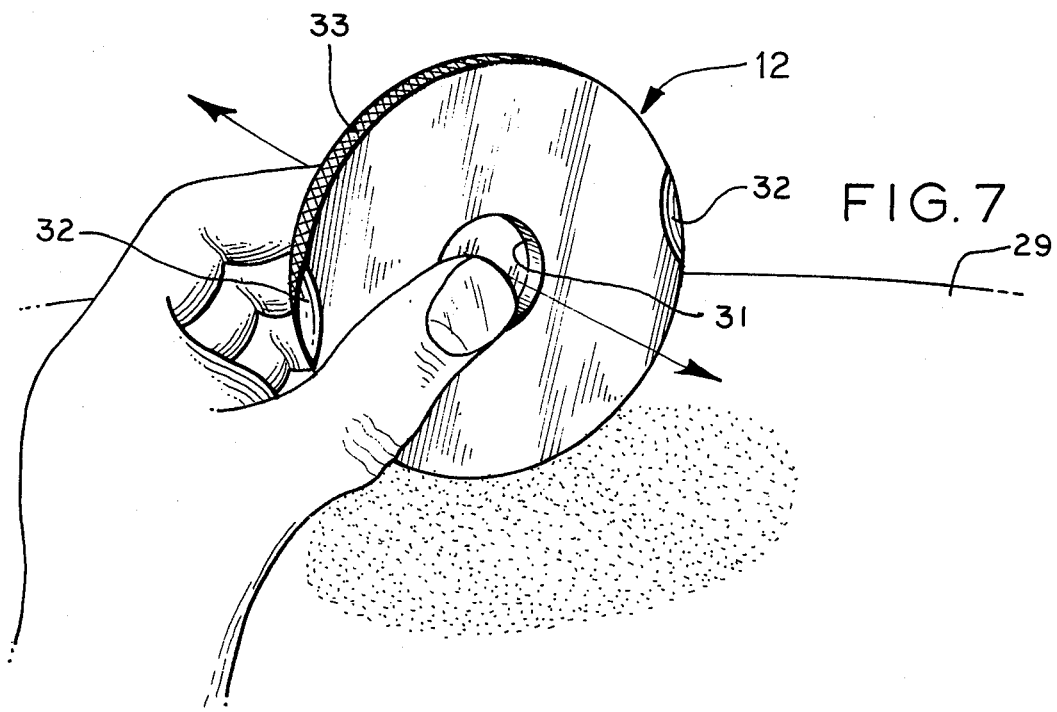

DIAGNOSTIC ELECTRODE ASSEMBLY WITH A SKIN PREPARATION SURFACE

BACKGROUND OF THE INVENTION

The present invention relates generally to disposable electrodes, and more particularly to an improved skin contact electrode assembly for detecting cardiac and other low level electrical signals generated within the human body.

Skin contact electrodes find extensive use for detecting and transforming potentials generated within the body into electrical signals which may be monitored for a variety of functions, such as the preparation of electrocardiograms and electroencephalograms. In recent years, with the advent of portable and more sophisticated EKG and other types of biomedical monitoring equipment, disposable electrode assemblies, wherein a metallic electrode and an electrolyte gel, together with an adhesive for holding the electrode in position, are combined in a unitary assembly for one-time use, have come into wide use. Not only do these assemblies avoid the time-consuming processes of applying gel and strapping the electrode in position, but they also avoid the necessity of cleaning the electrode after each use.

One disposable electrode assembly which has provided particularly good results is that claimed and described in the copending applications of Gregor Dean Long, Ser. No. 512,589, filed Oct. 7, 1974; William Garrettson Ellis et al, Ser. No. 670,403, filed Mar. 25, 1976, which is a continuation of Ser. No. 512,588, filed Oct. 7, 1974, now abandoned; William Garrettson Ellis, Ser. No. 670,404, filed Mar. 25, 1976, which is a continuation of Ser. No. 512,586, filed Oct. 7, 1974, now abandoned; and Charles W. Daugherty et al, Ser. No. 694,055, filed June 7, 1976, which is a continuation of Ser. No. 512,587, filed Oct. 7, 1974, now abandoned, all of which are assigned to the present assignee. This electrode assembly includes a relatively thin base member having a central hub portion and an adhesive-coated undersurface, a conductive gel-impregnated sponge contact contained in a downwardly facing recess located in the hub, and a relatively thick and inflexible cover member coextensive with the basic member. In storage the cover member is attached to the undersurface of the base member by the adhesive and the sponge is confined within the recess. Prior to use the base member is peeled away from the cover member to expose the adhesive surface, which when applied to a skin surface holds the sponge contact in compression-contact therewith. The present application is directed to an improvement in the electrode assembly wherein the cover member is provided with a roughened surface for use in preparing the skin surface to which the base member is to be applied.

SUMMARY OF THE INVENTION

The invention is directed, in a disposable electrode assembly for establishing an electrical connection to an adjacent skin surface, which includes a relatively flat thin base member formed of electrically non-conductive material and having an outside surface and an inside surface, and a raised center portion on the outside surface including a first recess forming a first open-ended chamber on the outside surface and a second recess forming a second open-ended chamber on the inside surface, and means comprising an electrically conductive terminal having an upper portion in the first chamber and a lower portion in the second chamber for establishing an electrically conductive path therebetween, the upper portion being adapted to receive a connecting terminal, and means comprising a sponge-like contact member saturated with electrically conductive fluid disposed within the second chamber for establishing an electrically conductive path between the lower portion of the terminal and the adjacent skin surface, and a relatively thick cover member having an inside surface substantially coextensive with the base member and being, overall, thicker than the base member, including an adhesive layer on the inside surface of the housing for holding the inside surface of the cover member against the inside surface of the base member when the electrode assembly is in storage, the base member being peelable away from the cover member to expose the inside surface of the base member for application to the skin surface, the adhesive holding the base member against the adjacent skin surface to enable the sponge-like contact member to establish electrical contact therewith, to the improvement comprising a roughened surface on the cover member for cleaning the skin surface prior to application of the electrode assembly.

BRIEF DESCRIPTION OF THE DRAWINGS

The features of the present invention, which are believed to be novel, are set forth with particularity in the appended claims. The invention, together with the further objects and advantages thereof, may best be understood by reference to the following description taken in connection with the accompanying drawings, in the several figures of which like reference numerals identify the elements, in which:

FIG. 5 is a cross-sectional view of the electrode assembly showing the assembly in position on an underlying skin surface with a mating electrical connector shown in phantom.

FIG. 6 is an enlarged perspective view of the backing member showing a roughened skin preparation surface provided thereon in accordance with the invention.

FIG. 7 is a perspective view showing the cover member being used for preparing the underlying skin surface.

DESCRIPTION OF THE PREFERRED EMBODIMENT

Figure 1:
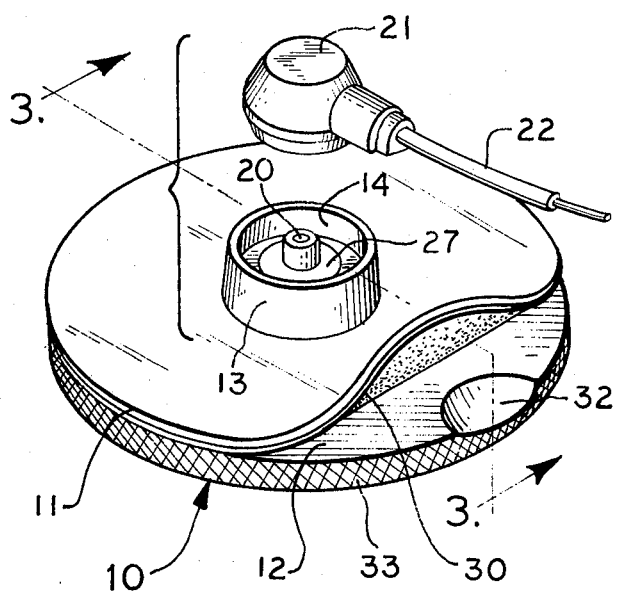
FIG. 1 is a perspective view of an electrode assembly constructed in accordance with the invention showing the base member partially peeled away from the backing member and showing a mating electrical contact for establishing electrical contact with the assembly.
Figure 2:
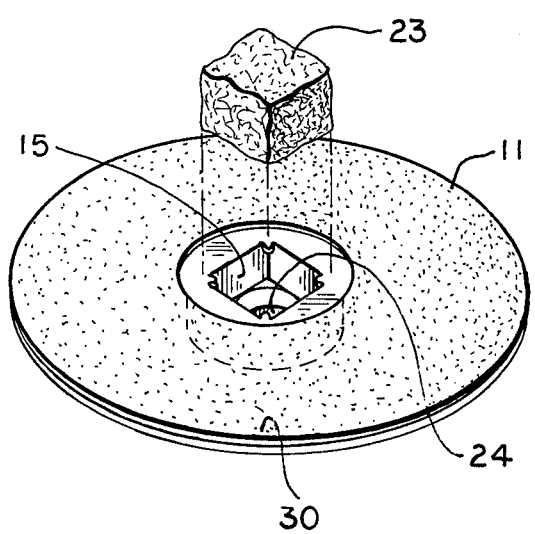
FIG. 2 is a perspective view of the electrode assembly inverted showing the sponge-like skin contact member of the assembly removed from its recess in the inside face of the transparent base element of the assembly.
Figure 3:
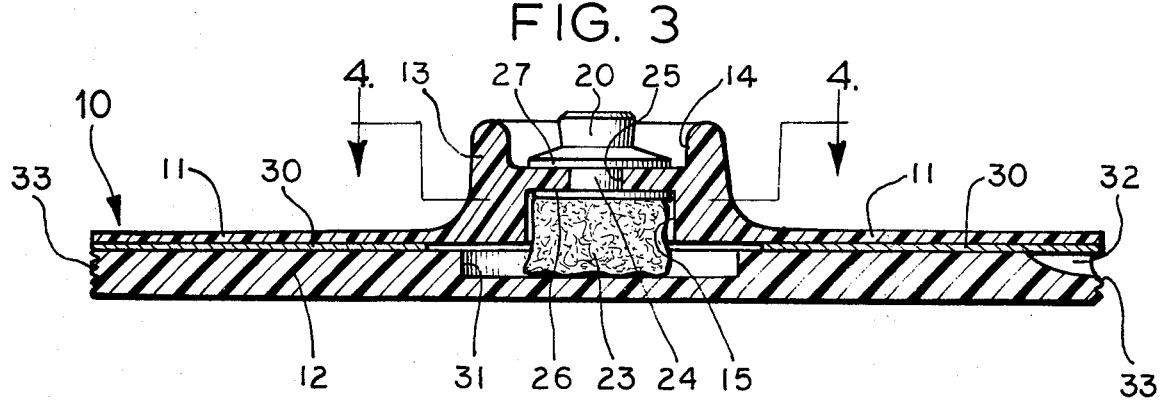
FIG. 3 is a cross-sectional view taken along lines 3—3 of FIG. 1 showing the cover element of the electrode assembly in position for storage.
Figure 4:
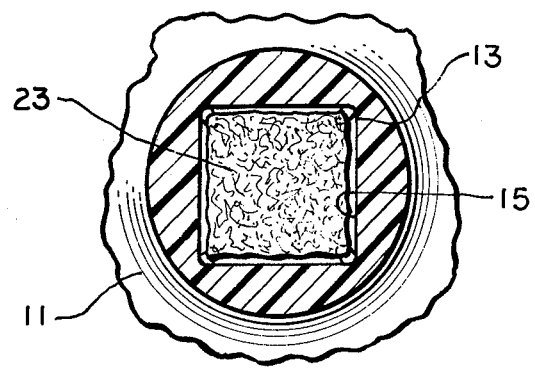
FIG. 4 is an enlarged cross-sectional view taken along lines 4—4 of FIG. 3 showing the raised or hub portion of the base member of the assembly.

Referring to the figures, and particularly to FIGS. 1-3, an electrode assembly 10 incorporating the features of the present invention is seen to comprise a relatively thin flexible disc-shaped base member 11 formed or molded of a transparent non-conducting material such as plastic, and a relatively thick and inflexible disc-shaped cover member 12 of like diameter formed or molded of an opaque plastic material. The top (FIG. 1) or outside surface of the base includes a central raised or hub portion 13 which includes an upwardly facing open-ended bore or chamber 14, and the bottom or inside surface of the base includes a four-sided downwardly-facing open-ended chamber 15.

To facilitate electrical connection to an associated monitoring apparatus, an electrical snap-type connector terminal 20 is provided within chamber 14. This terminal, which may be of conventional design and construction, includes a slightly tapered upwardly extending cylindrical portion which engages complementarily dimensioned inwardly-biased downwardly-extending contact fingers (not shown) on a female connector 21, which also may be conventional in design and construction. The effect of the open-ended chamber 14 is to form a socket wall around terminal 20 which prevents inadvertent contact with the electrical circuit established therethrough and consequent erroneous output signals, and to provide in conjunction with the terminal a socket for receiving connector 21. Connector 21 is connected by an insulated conductor 22 of appropriate length to the monitoring apparatus.

Electrical contact is made to the patient's skin by means of a compressible body contact member 23, which may be fabricated from a sponge-like material impregnated with an electrically conductive gel. While the body contact 23 can be formed in various shaped and dimensions, it is preferably sized to fit within and occupy substantially the entire inside volume of chamber 15 to achieve the largest possible skin contact area for the lowest possible contact resistance. To this same end, the vertical dimension (in FIGS. 3 and 5) of contact 23 is preferably such that the contact member is under compression when the inside surface of base 11 is pressed against the skin surface, as shown in FIG. 5.

An electrical connection is established between the sponge-like body contact 23 and terminal 20 by means of a rivet-shaped electrically conductive retaining member 24 which extends between the rear wall of chamber 15 and the bottom of terminal 20. The retaining member 24 extends through an aperture 25 provided in base 11 between chamber 15 and chamber 14, and into a locking press-fit engagement with terminal 20. A flange portion 26 at the bottom end (as viewed in FIGS. 3 and 5) of member 24 prevents the member from being pulled through aperture 25 and provides increased contact area for establishing a low resistance electrical connection with body contact 23. A similar flange portion 27 on contact 20 prevents that member from being pulled through aperture 25, so that once members 20 and 24 have been press-fit together during manufacture of the electrode assembly a very secure electrically-integral attachment between the contacts and base 11 is obtained.

Referring to FIG. 3, while being stored prior to use the disc-shaped cover plate 12 overlies the interior surface of base 11 and is attached thereto my means of an adhesive layer 30, which preferably comprises an acrylic-based adhesive of a type which does not promote allergic reactions or irritation to the skin, is deposited on both sides of a thin transparent disc-shaped polyethylene carrier formed of polyethylene or similar material with is provided with a central aperture so as not to overlie the open end of chamber 15. The adhesive layer 30 is sandwiched between the interior surface of base 11 and cover 12 to hold the two elements together, and cover member 12 is preferably provided with an open-ended chamber or recess 31 on its inside surface to allow partial expansion of the sponge-like skin contact 23 during storage. This enables the sponge to retain a greater quantity of conductive gel during storage, and consequently to release a greater amount of gel onto the underlying skin surface when compressed prior to use.

Prior to applying the electrode assembly 10 to a skin surface, the thin flexible and transparent base member 11 is peeled away from the relatively stiff cover member 12 to expose the adhesive surface 30, as shown as FIG. 1. To facilitate removal of the cover member a thumb recess 32 may be provided along the circumferential margin of cover 12. Since the cover is formed of thicker and less flexible material than the base 11, peeling the base member away from the backing member can be readily accomplished once the cover is initially separated by means of recess 32.

The skin surface to which the electrode is to be applied is next prepared by rubbing it with a roughened surface so as to clean away dirt and foreign particles and to remove dried skin particles which might reduce surface conductivity. In accordance with the invention, this skin preparation is facilitated by the provision of a roughened surface 33 on the cover member 12. In use this surface, which may consist of a plurality of closely spaced serrations on the edge of cover 12, as shown in FIGS. 1, 3, 6, and 7, is placed against and rubbed rapidly over the skin surface in the manner shown in FIG. 7. In addition to performing this skin preparation operation the abrasive surface also facilitates the handling of cover 12 and the peeling away of base 11.

As evident in FIG. 7, the flat disc-shaped cover member 12 can be readily grasped by a user such that the roughened edge 33 can be brought to bear against the underlying skin surface 29. By reason of the roughened surface being located on the edge of the disc-shaped cover member the user is offered an unobstructed view of the skin surface, allowing for more accurate and thorough preparation, even in poorly lit working areas. Furthermore, since the roughened edge extends through the entire periphery of the cover member, no particular alignment of the cover member is required.

Various patterns may be molded into cover 12 to form the abrasive surface 33. For example, serrations may be provided in an axially-aligned closely-spaced arrangement, or in a criss-cross pattern on the rim of cover. Alternatively, a random sandpaper-like surface may be molded into the rim.

The electrode assembly is applied by pressing the inside surface of the base member 11 to the skin surface 29, as shown in FIG. 5. This compresses the sponge-like skin contact member 23 and releases conductive gel onto the underlying roughened and cleaned skin surface, thereby establishing a low-resistance electrical connection through member 23 to the body. The adhesive layer 30, which substantially coextensive with the interior surface of base 11, adheres to the skin to hold the electrode assembly in position. To accomplish this the area of the adhesive 30 on the interior surface of base 11, and hence the diameter of the base, must be sufficiently large to obtain an adequate adhesive force, taking into consideration that the adherence of the adhesive to the skin must not be so great as to cause unnecessary discomfort to the patient when the electrode assembly is removed.

In a preferred embodiment of the invention the base member 11 is preferably fabricated of a transparent flexible polymer, co-polymer or tri-polymer plastic, or other suitable rubber-like material. One material which has proved successful for this application is polyvinyl chloride. The cover member 12 may be formed of a hydrophylic material such as polyethylene and may have color added to color code the electrode during storage. The sponge-like skin contact 23 may be formed of a polyether polyurethane foam impregnated with an ionic fluid in a suitable organic based gel, for example, that currently available from Parker Laboratories, Inc. under the trademark Spectra 360 or that available from Pharmaceutical Innovations, Inc. under the trademark LECTRON II, although other conductive fluids or gels may be used without departing from at least the broader principles of the present invention.

To prevent the gel-impregnated contact 23 from being attracted to the cover 12 as the base 11 is peeled away, the base is preferably formed of a material which is more hydrophylic than the cover. This is believed to cause the gel-impregnated sponge to be attracted to the base to a greater extent than it is attracted to the cover, and therefore to remain with the base. The snap terminal 20 and retaining member 24 are preferably formed of silver, silver-coated brass, brass, rhodium-coated brass, nickel or zinc-coated brass, although other conductors may be employed. Silver coating is preferred because it has the lowest half cell potential and therefore generates the least spurious signal with relative motion of contacts 20 and 21 as the patient moves.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. A disposable electrode assembly for establishing an electrical connection to an underlying skin surface comprising, in combination:
   a relatively flexible base member formed of electrically-insulating material having an outside surface and an inside surface;
   contact means on said base member for establishing electrical contact with said underlying skin surface, said contact means including a first contact portion on said outside surface and a second contact portion in electrical communication with said first contact portion on said inside surface;
   a cover member having an inside surface substantially coextensive with said inside surface of said base member, said cover member being, overall, substantially less flexible than the major extent of said base member and including a circumferential edge portion;
   an adhesive layer on said inside surface of said base member holding said inside surface of said cover member against said inside surface of said base member so as to increase the rigidity of said electrode assembly during storage, said base member being peelable away from said cover member to enable said adhesive layer to be placed in contact with said underlying skin surface to hold said second contact portion in contact with said skin while said electrode assembly is in use; and
   means including an abrasive surface on at least a portion of said circumferential edge portion of said cover member for use in preparing said underlying skin surface prior to application of said second contact portion thereto.

2. A disposable electrode assembly as defined in claim 1 wherein said cover member is generally disc shaped.

3. A disposable electrode assembly as defined in claim 1 wherein said cover member is generally cylindrical in form and includes a side wall, and said abrasive surface is disposed on said side wall.

4. A disposable electrode assembly for establishing an electrical connection to an underlying skin surface comprising, in combination:
   a base member formed of electrically-insulating material having an outside surface and an inside surface;
   said base member including a raised hub portion on said outside surface and a relatively flexible flange portion surrounding said hub portion, said hub portion including a recess forming an open-ended chamber on said inside surface, and a connecting aperture extending from said chamber to said outside surface;
   means comprising an electrically conductive terminal having a first portion on said outside surface, a second portion in said open-ended chamber, and a third portion extending through said connecting aperture, said first portion being adapted to receive a connecting terminal;
   means comprising a sponge-like contact member saturated with electrically conductive fluid disposed within said chamber in contact with said second portion of said terminal for establishing an electrically conductive path between said terminal and said adjacent skin surface;
   a generally disc-shaped cover member having an inside surface substantially coextensive with said inside surface of said base member, said cover member being, overall, substantially less flexible than said flange portion of said base member and including a circumferential edge portion;
   an adhesive layer on the inside surface of said base member holding said inside surface of said cover member against said inside surface of said base member so as to enclose said sponge-like contact member within said open-ended chamber and increase the rigidity of said electrode assembly during storage, said base member being peelable away from said cover member to enable said adhesive layer to be placed in contact with said underlying skin surface to hold said sponge-like contact member in contact with said skin while said electrode assembly is in use; and
   means including an abrasive surface on said circumferential edge portion of said cover portion for use in preparing said underlying skin surface prior to application of said contact member thereto.

5. A disposable electrode assembly as defined in claim 4 wherein said cover member is generally cylindrical in form and includes a side wall, and said abrasive surface is disposed on said side wall.

6. In a disposable electrode assembly for establishing an electrical connection with an underlying skin surface, said electrode assembly comprising a relatively flexible base member formed of electrically-insulating material defining an outside surface and an adhesive carrying inside surface, said base member carrying an electrically conductive terminal on said inside surface and adapted for holding said terminal in contact with the skin, said terminal communicating with said outside surface, and a cover member being, overall, substantially less flexible than the major extent of said base member, said cover member having an inside surface attached to and being substantially coextensive with said adhesive carrying surface so as to enclose said terminal and increase the rigidity of said electrode assembly during storage, and further having a circumferential edge portion, the improvement wherein said cover member includes an abrasive surface on at least a portion of said circumferential edge portion to facilitate preparation of said underlying skin surface prior to said adhesive layer being placed in contact with said skin surface to hold said electrically conductive terminal in contact therewith while the electrode assembly is in use.

7. A disposable electrode assembly as defined in claim 6 wherein said cover member is generally disc shaped.

8. A disposable electrode assembly as defined in claim 6 wherein said cover member is generally cylindrical in form and includes a side wall, and said abrasive surface is disposed on said side wall.

* * * * *